(12) United States Patent
Staples et al.

(10) Patent No.: US 7,669,489 B2
(45) Date of Patent: Mar. 2, 2010

(54) METHOD AND APPARATUS FOR LIQUID CHROMATOGRAPHY AUTOMATED SAMPLE LOADING

(75) Inventors: Kary J. Staples, DeForest, WI (US); Luke D. Roenneburg, Albay, WI (US)

(73) Assignee: Gilson, Inc., Middleton, WI (US)

( * ) Notice: Subject to any disclaimer, the term of this patent is extended or adjusted under 35 U.S.C. 154(b) by 802 days.

(21) Appl. No.: 11/404,312

(22) Filed: Apr. 14, 2006

(65) Prior Publication Data

US 2006/0179924 A1 Aug. 17, 2006

Related U.S. Application Data

(62) Division of application No. 11/015,284, filed on Dec. 17, 2004, now Pat. No. 7,055,402.

(60) Provisional application No. 60/531,444, filed on Dec. 19, 2003.

(51) Int. Cl.
*G01N 35/10* (2006.01)

(52) U.S. Cl. .................................. 73/864.24

(58) Field of Classification Search ....................... None
See application file for complete search history.

(56) References Cited

U.S. PATENT DOCUMENTS

| | | | |
|---|---|---|---|
| 3,604,267 A | 9/1971 | Johns | |
| 4,478,094 A | 10/1984 | Salomaa et al. | |
| 5,399,173 A * | 3/1995 | Parks et al. | 604/533 |
| 5,400,666 A * | 3/1995 | Song | 73/864.21 |
| 5,725,831 A * | 3/1998 | Reichler et al. | 422/56 |
| 6,207,031 B1 | 3/2001 | Adourian et al. | |
| 6,403,037 B1 | 6/2002 | Chang et al. | |
| 6,475,774 B1 * | 11/2002 | Gupta | 435/287.2 |
| 6,581,593 B1 * | 6/2003 | Rubin et al. | 128/202.27 |
| 6,783,649 B2 | 8/2004 | Hedberg et al. | |
| 6,787,111 B2 | 9/2004 | Roach et al. | |
| 2003/0225477 A1 | 12/2003 | Gilman et al. | |
| 2004/0033554 A1 | 2/2004 | Powers | |
| 2004/0137605 A1* | 7/2004 | McGarry et al. | 435/287.2 |
| 2005/0009101 A1* | 1/2005 | Blackburn | 435/7.1 |

OTHER PUBLICATIONS

International Search Report dated Nov. 4, 2005 for PCT/US2004/042356.

Office Action issued in corresponding Australian Patent Application No. 2004308278 dated May 18, 2009.

* cited by examiner

*Primary Examiner*—Robert R Raevis
(74) *Attorney, Agent, or Firm*—Foley & Lardner LLP

(57) ABSTRACT

A method for automated loading of liquid sample to a liquid chromatography testing device is provided including installing a disposable tip on a probe, moving the probe with an automated liquid handler to a loading position proximate to a sample, and drawing a sample into the disposable tip. The probe is then moved to an injection position proximate an injection port, and the sample is injected from the disposable tip into the injection port. Also provided are the novel injection ports. After injection of the sample, the disposable tip is then removed from the probe. These steps may be repeated a plurality of times to sequentially load a plurality of samples. An exemplary method of the invention is directed to use with a liquid chromatography apparatus. An apparatus for assisting in the removal of the disposable tip is also provided.

14 Claims, 9 Drawing Sheets

METHOD AND APPARATUS FOR LIQUID CHROMATOGRAPHY AUTOMATED SAMPLE LOADING

CROSS REFERENCE TO RELATED APPLICATION

This non-provisional application is a divisional application of U.S. patent application Ser. No. 11/015,284, filed Dec. 17, 2004, entitled METHOD AND APPARATUS FOR LIQUID CHROMATOGRAPHY AUTOMATED SAMPLE LOADING, the entire disclosure of which is hereby incorporated by reference in its entirety and for all purposes.

FIELD OF THE INVENTION

The present invention relates to methods for automated loading of samples, including automated loading of samples for liquid chromatography.

BACKGROUND

In laboratory and other applications, automated liquid handlers that transport liquid samples are used in a variety of laboratory procedures. One example of an automated liquid handler is disclosed in U.S. Pat. No. 5,988,236 ("the '236 patent") assigned to the assignee of the present application and incorporated herein by reference. The liquid handler of the '236 patent has a work bed that supports an array of sample containers, with multiple probes supported on an automated mover over the work bed. The automated mover is capable of moving the probes into alignment with one or more sample containers on the work bed to carry out liquid handling operations. Another example of a liquid handler can be found in U.S. Pat. No. 4,422,151, incorporated herein by reference.

Liquid chromatography, including high-performance liquid chromatography (HPLC), is one example of an application in which automated liquid handlers are used. Liquid chromatography is useful in characterizing a sample through separation of its components by flow through a chromatographic column, followed by detection of the separated components with a flow-through detector. Some HPLC systems include an automated liquid handler to load samples. In these systems, the liquid handler moves probes to load samples from sample containers and then inject the samples into an injection port. A metal needle may be attached to the probe to facilitate extraction of the sample from the container and injection of the sample into the injection port.

Although HPLC and other chemical test systems that include automated liquid handling are known, many long standing problems remain unresolved. As an example of an unsolved problem in liquid handling, carryover from one sample to subsequent samples can cause test contamination and inaccuracy when using many liquid handlers.

Carryover occurs when residue of a first sample remains in or on the probe or in the injection port and is then mixed with a subsequent sample. To reduce carryover, automated liquid handlers in chromatography and other test systems typically perform two solvent flushes between samples. A first flush is performed with the probe in the injection port to flush the port and the lines connected thereto. The probe and needle are then removed from the injection port, moved to a flushing position, and flushed a second time. Even with flushing, however, some carryover may occur. Additional flushing reduces carryover but slows processing and adds cost.

Another example of a problem connected with automated liquid handling methods in chromatography includes the presence of dead space associated with the samples. Dead space is an artifact of the type of sample injection system. Generally, samples are injected using a pressure differential that may include a driving force of air or inert gas and/or a drawing force of vacuum. In chromatography, the amount of sample that can be injected, called the test sample volume capacity also may be referred to as the test loop volume. Concerning the loop volume, known injection methods generally using known injection ports, probes and needles can result in considerable foreign material such as air being present in the test loop volume. For instance, in known injection methods, if the flow through a loading needle is too slow, or if a good seal is not provided between a probe needle and the injection port, air or other foreign material may be loaded on the chromatography instrument. To minimize the risk of not enough sample and too much foreign material, an excess of sample is typically loaded in the probe and injection port. In order to successfully load the correct amount of sample, known automated loading methods may require about four times or more of test loop volume to ensure that no inert gas or void space is injected. This amount of excess volume adds expense and time to testing, not to mention that the excess wastes valuable sample.

Still another known problem in automated handling for chemical analysis relates to the lack of reproducibility of volumetric measurements. An advantage to accurate volumetric measurements includes desirably minimizing specific variations in sample volume from test to test. However, methods to determine volumetric accuracy using known probes and attached needles is limited.

This invention also solves an additional problem found with many conventional HPLC systems. In many liquid handling applications including HPLC, bio-compatible components are required. Although some systems use pumping and injection valves made from biocompatible PEEK or biocompatible titanium, there is ultimately still a non-compatible component (often stainless steel) in the injection needle. In order to mask the non-compatible element, the injection needles may be either coated or made from titanium to reduce the metallic component. However, these modifications fail to reduce carry over and when coated injection needles are used, problems can arise as the coating wears.

SUMMARY OF THE INVENTION

An embodiment of the present invention is directed to a method for automated loading of a liquid sample to a liquid chromatography testing device and includes the steps of installing a disposable tip on a probe supported on an automated mover, moving the probe with the automated mover to a loading position proximate to a sample container, and drawing a sample from the container and into the disposable tip. The probe is then moved with the automated mover to an injection position proximate an injection port, and the sample is injected from the disposable tip and into the injection port. The disposable tip is then removed from the probe. Preferably, these steps are repeated a plurality of times to sequentially load a plurality of samples. Because the use of a disposable tip that is removed after use substantially eliminates carryover between loadings, the two-step flushing procedure between loadings may be replaced with a single flush procedure to result in time and cost savings. An exemplary method of the invention is directed to use with a liquid chromatography system. Additionally, in some embodiments, a specialized probe guide that allows removal of the used disposable tip, as well as a waste receptacle for collecting the used disposable tips, are described.

Furthermore, certain methods of the present invention allow use a smaller loop volume to test samples. The use of a smaller loop volume dramatically reduces the amount of sample that must be used for each test. In some embodiments, the lower loop volume will be a result of the sealing fit between a disposable tip and an injection port.

BRIEF DESCRIPTION OF THE DRAWINGS

FIG. 6 also demonstrates the waste receptacle as attached to the workbed of the liquid handler.

DETAILED DESCRIPTION

Figure 1:
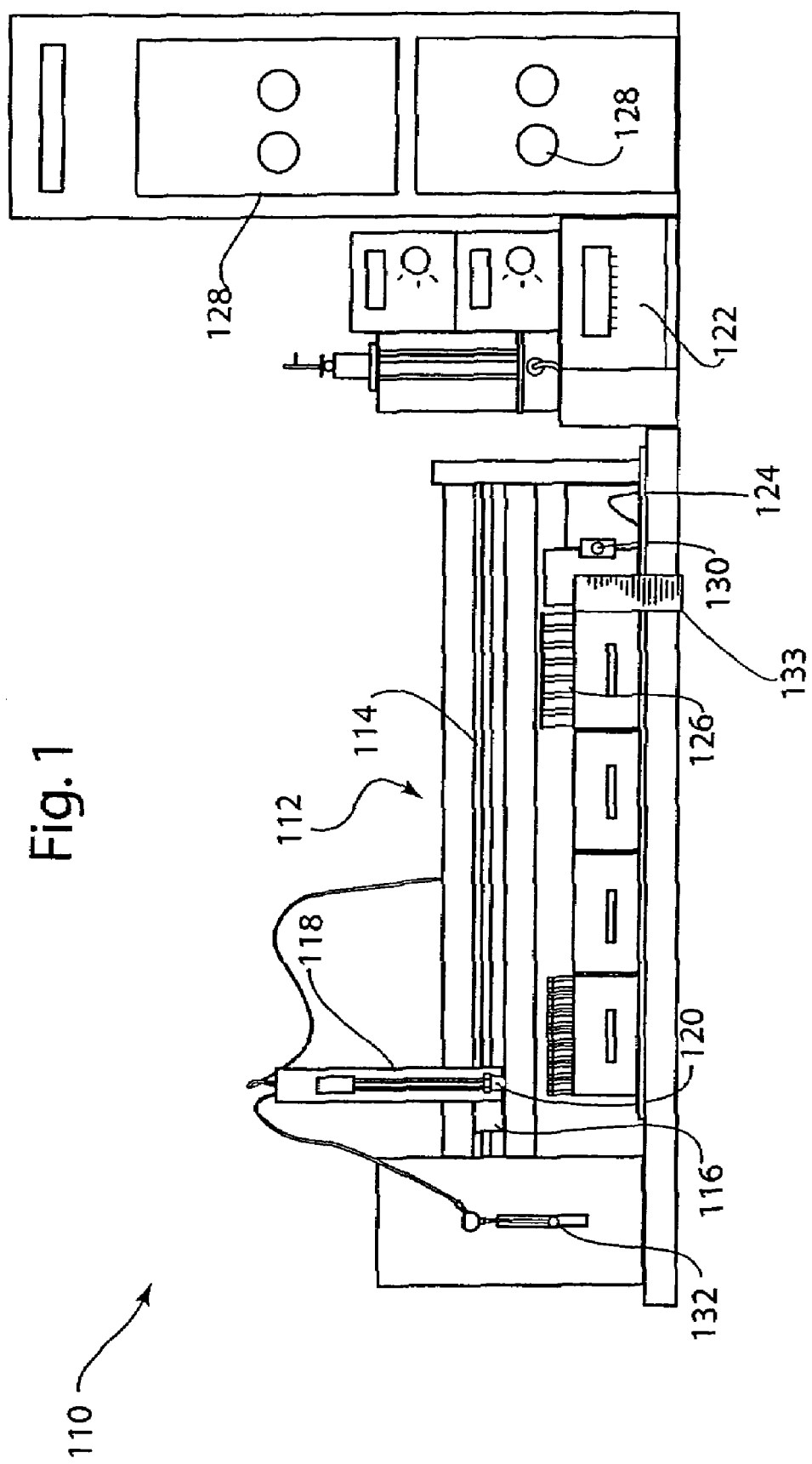
FIG. 1 shows an HPLC system including an automated liquid handler that is useful for practice in some embodiments of the invention.

Having reference now to the drawings, FIG. 1 is a perspective view of a liquid chromatography testing device used in performing an exemplary method of the invention. Specifically, FIG. 1 shows a high-pressure liquid chromatography ("HPLC") system generally at 110. One of skill in the art will understand that although the embodiments of the invention are shown during use with an HPLC system, the present invention is applicable to any type of liquid handler requiring aspiration and dispension of sample. In the embodiment of FIG. 1, the HPLC system 110 includes an automated liquid handler, or "XYZ mover," shown generally at 112. The automated liquid handler includes a track 114, an arm 116 that runs in a first direction (i.e., "X" direction) along the track 114, and a probe carrier 118 that runs in a second direction (i.e., "Y" direction) along the arm 116. Generally, any automated liquid handler that is capable of motion in the X, Y, and Z directions can be used with the invention. The probe carrier 118 supports one or more probes 120 that are operable to move in a vertical direction (i.e., "Z" direction). In some embodiments, the probes may be generally cylindrical stainless steel. The skilled artisan will understand that the material used to make the probe of the present invention is not particularly limiting. Further, the shape of the probe may be any shape as long as the probe is capable of fitting both a disposable tip and an injection port. A controller 122 that includes a processor controls the movement of the automated liquid handler 112. The controller 122 may also control liquid pumping including aspiration and dispensing of sample and other liquid. In some embodiments, the controller will include proprietary HPLC system software. This software may be a PC based software program or a keypad program. A keypad when used with a keypad program can consist of any variety of keypads such as PALM® type devices. The controller 122 may be linked to a computer device (not shown) that is separate from the HPLC system 110. In some embodiments, the computer device will be integral to the HPLC system. Generally, a plurality of sample containers 126 will be supported on the workbed 124. However, it should be understood that the number of sample containers shown in FIG. 1 are for demonstration purposes only and the actual number of sample containers can be as few as one or as many as can be held by the workbed. Furthermore, although it may be advantageous to use sample containers known in the art, one of skill in the art will understand that the sample containers that can be used with the invention are not so limiting. The sample containers can be made of any material and can be in any shape as long as they can be received by the workbed and used with the methods and apparatus of the present invention.

The HPLC system 110 also includes several high-pressure liquid chromatography (HPLC) modules 128. Each of the HPLC modules 128 is linked to an injection port 130 so that samples input into the injection port 130 may be communicated to the modules 128 for testing. In the embodiment shown in FIG. 1, the HPLC modules and the injection ports 130 are also linked to the controller 122. Further, one or more syringe pumps 132 may be linked to the controller and communicate through one or more valves and fluid lines with the probes 120 and the HPLC modules 128.

Figure 2:
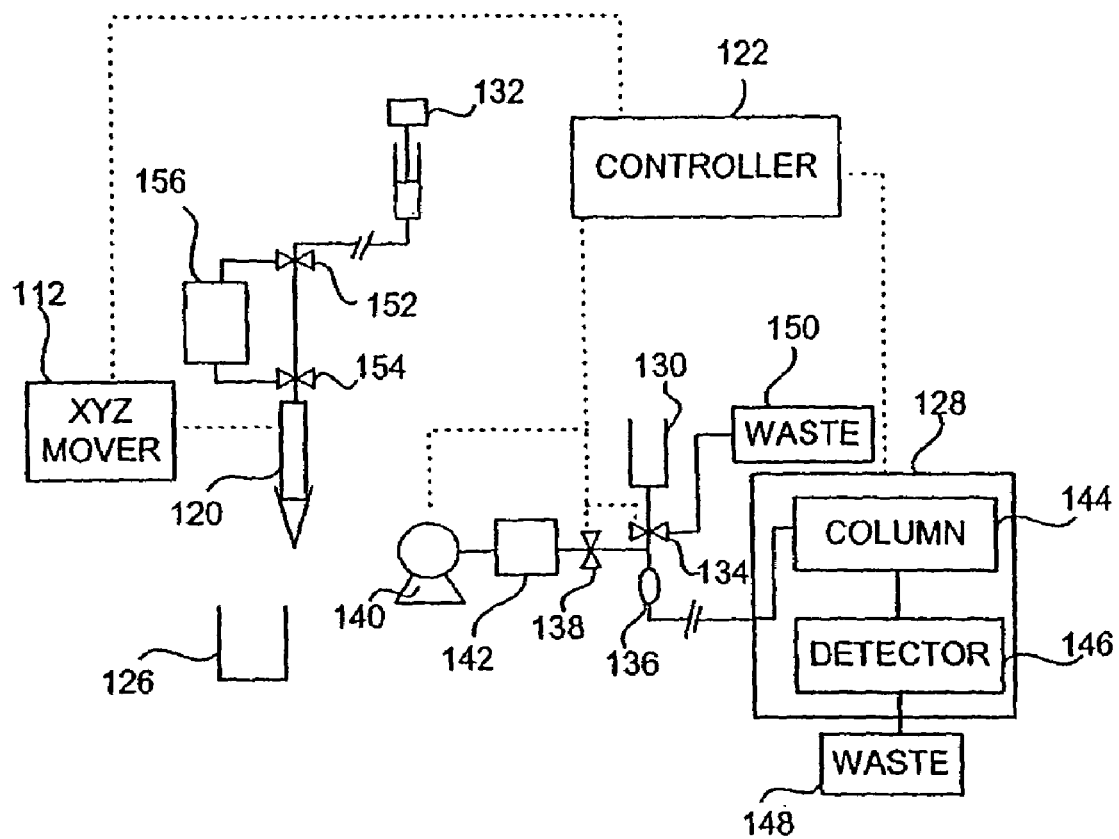
FIG. 2 is a schematic diagram of the HPLC system of FIG. 1.

The schematic of FIG. 2 illustrates operation of an embodiment of the HPLC system 110 and its various elements. The controller 122 controls the automated liquid handler 112 to direct the probe 120 to draw a sample from a selected sample container 126. In certain embodiments, the controller 122 may operate a syringe pump 132 to cause a desired volume of sample to be drawn from the selected sample container 126, and then cause the automated liquid handler 112 to move the probe 120 to the injection port 130. The controller 122 may then direct the syringe pump 132 to exert a positive pressure to force the sample from the probe 120 into the injection port 130, and into a test sample volume receptacle or "sample loop volume receptacle" 136.

Once the sample is in the sample loop volume receptacle 136, the controller 122 may manipulate the two-way six-port valve 134 to isolate the injection port 130 from the loop 136, open a valve 138, and activate the pump 140 to force liquid phase carrier fluid from a reservoir 142 upstream of the sample loop 136. The skilled artisan will understand that although a two-way six-port valve is demonstrated in the figures, any type of a valve, including, but not limited to, a two-way ten-port valve and a six-way six-port valve may be used with the invention as long as there is a connected suitable injector port. Further, the pump 140 may be a piston or other type of pump. The carrier fluid carries the sample to be tested from the sample loop 136 into the HPLC module 128 and the HPLC column 144 and detector 146 for analysis. The controller 122 may then initiate the HPLC module 128 to analyze the sample. When used with the methods and apparatus of the invention, a sample may include any number of organic or biological samples in varying degrees of costic solvents. In certain embodiments, this could include biologicals such as whole blood, plasma, and urine derived compounds. Further, not biological compounds such as highly acidic or basic solutions including but not limited to tri-fluoro-acetic acid (TFA), sulfuric acid, formic acid, glacial acetic acid, and concentrated sodium hydroxide may be used with this invention without any detrimental effects to the injection process. After testing the sample, the controller 122 may direct disposal of the sample in a waste container 148.

With the two-way six-port valve 134 linking the injection port 130 to a flush waste container 150, the controller may operate the valves 152 and 154 to open flow from the syringe pump 132 to a solvent reservoir 156. Positive pressure from the syringe pump 132 will then drive a flushing solvent through the probe 120, the injection port 130, the three way valve 134 and into the flush waste container 150, thereby cleaning these components for use in a subsequent test.

Figure 1A:
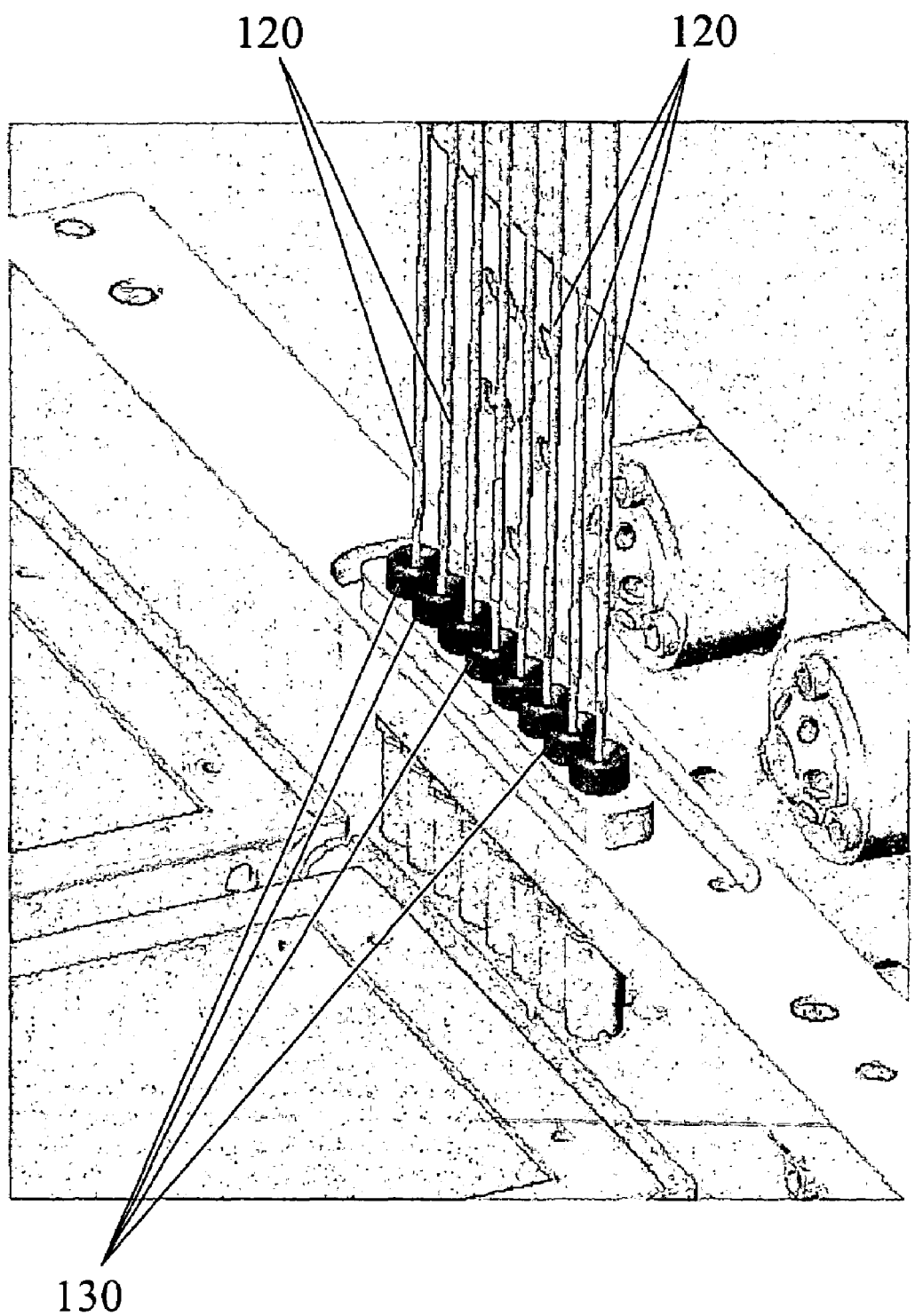
FIG. 1a shows an HPLC system-including a plurality of probes and injection ports in accordance with an exemplary embodiment.

Those skilled in the art will appreciate that the schematic of FIG. 2 and related discussion herein illustrates only one of many possible configurations and methods for performing automated sample loading of HPLC test samples. Many variations and alternates may also be practiced. For example, a plurality of probes 120 and a plurality of injection ports 130 may be provided as shown with reference to FIG. 1a. A detailed example of one alternate automated HPLC sample loading configuration and method can be found in the commonly owned U.S. patent application Ser. No. 10/075,811.

Having described a device useful to practice a method of the invention, one embodiment method shown in the flowchart of FIG. 3 may now be described. The method includes mounting a disposable probe tip on a probe 120 (block 302). With reference again to FIG. 1, this method may include using the automated liquid handler 112 to move one or more of the probes 120 to a position above an array of disposable tips held on a rack or support 401 on the workbed 124, and then to lowering the one or more probes 120 into engagement with the one or more disposable tips.

Figure 4A:
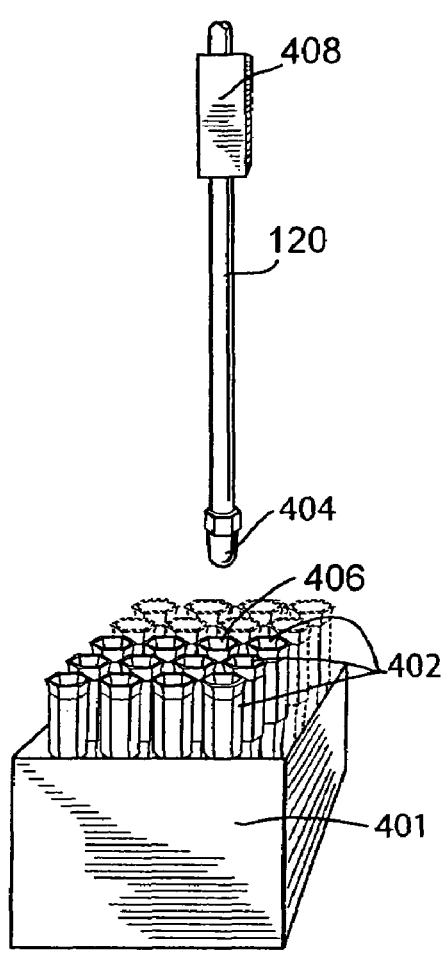
FIGS. 4A, 4B and 4C illustrate mounting a disposable tip on a probe.
Figure 4B:
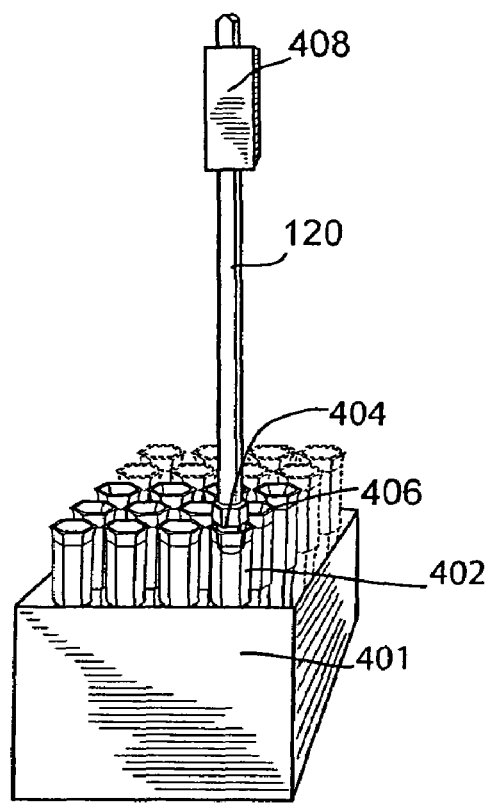
Figure 4C:
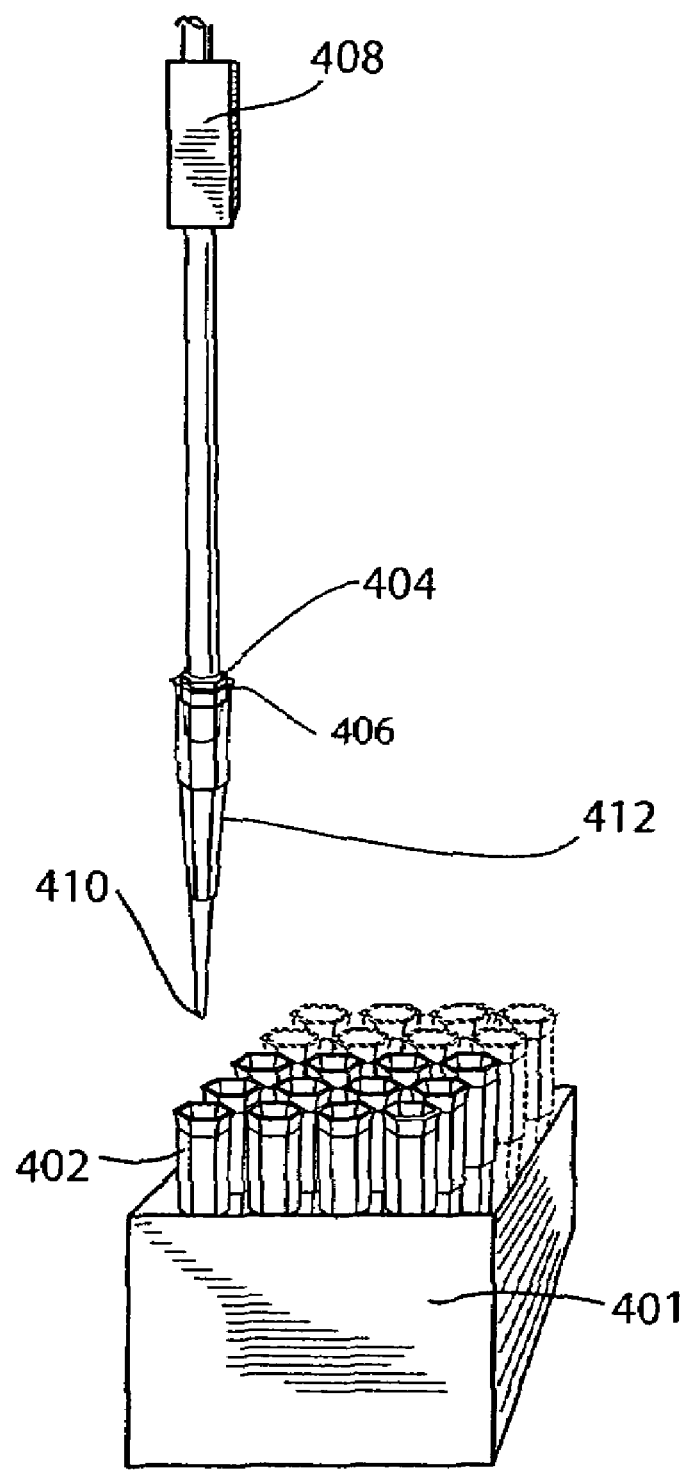

FIGS. 4A, 4B and 4C are useful to further illustrate the mounting of the disposable tip. In the embodiment shown in FIGS. 4A, 4B and 4C, the disposable tip is mounted on the prove using frictional engagement. FIG. 4A shows a multitude of probes being lowered towards a support 401 that holds a plurality of disposable tips 402 generally arranged in an array. Each probe 120 has a probe insertion end 404, and each of the disposable tips has a mouth 406 for receiving the probe insertion end 404. One of skill in the art will understand that that insertion end of the probe and the mouth of the disposable tip may be of any shape as long as the two pieces can fit together and the disposable tip can later be removed. FIG. 4A also shows a probe guide 408 through which the probe 120 slideably moves in a vertical direction. FIG. 4B illustrates the probe insertion end 404 having been inserted into the disposable tip mouth 406 to frictionally engage the disposable tip 402. FIG. 4C illustrates the probe 120 being lifted with the disposable tip 402 frictionally engaged on the probe insertion end 404. Although in many embodiments, the disposable tip will be mounted on the probe using frictional engagement, any form of mounting the disposable tip on the probe that allows removal of the disposable tip using the methods and apparatus of the present invention may be used.

As best illustrated in the view of FIG. 4C, in one embodiment, the disposable tips 402 are generally cone shaped, and have a disposable tip outlet 410 opposite from the wider disposable tip mouth 406. A disposal tip wall 412 connects the disposable tip mouth 406 to the disposable tip outlet 410. In certain embodiments, the disposal tip wall will be generally cone-shaped. In many embodiments, the disposable tip 402 is made of a plastic or other resilient material selected for considerations such as chemical resistance and compatibility, durability, cost, and the like. In some embodiments, the disposable tip 402 is made of a hydrophobic material. Non-limiting examples of disposable tip 402 materials include polypropylene, polytetrafluoroethylene (PTFE), and similar polymers. However, a disposable tip may be made from any acceptable material. Generally as used herein a disposable tip encompasses any tip that is used only for a single sample and is not meant to be limiting to the disposable tips currently commercially available.

Figure 3:
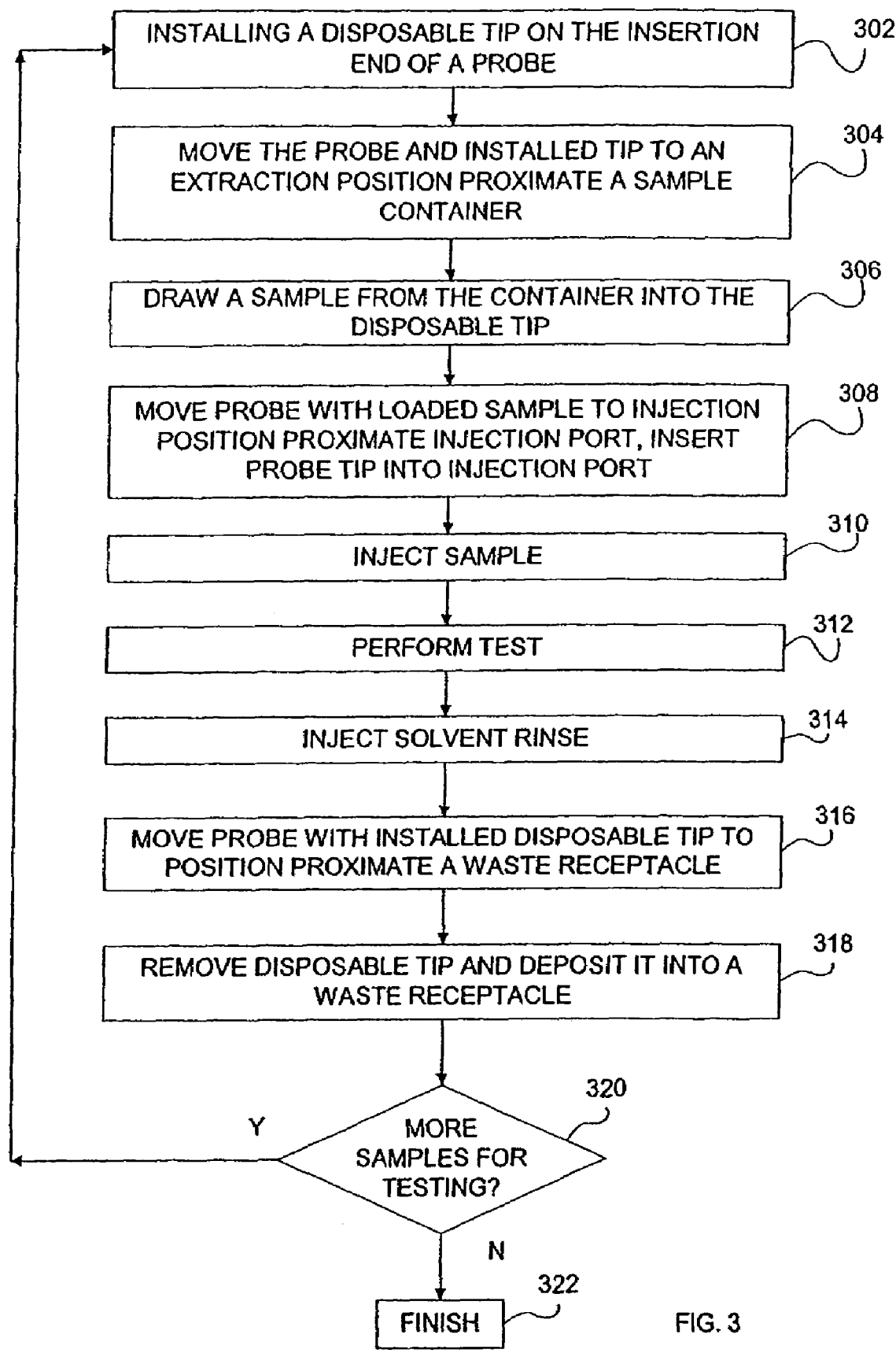
FIG. 3 is a flowchart of a method of the invention.

Referring to the flowchart of FIG. 3, subsequent to mounting the disposable tip on the probe, one embodiment of the invention includes moving the probes 120 with mounted disposable tips 402 (as generally shown in FIG. 4C) to a sample loading position proximate a selected sample contained in a sample container 126 or containers (block 304). With reference to FIG. 1, this step may entail moving the probe 120 with the automated liquid handler 112 in X, and/or Y, and/or Z directions relative to one or more sample containers 126 present on the workbed 124 in order to align the probe with the sample. Following the alignment of the probe, a sample may then be loaded from the sample container 126 into the disposable tip 402 (block 306). This may be accomplished, for instance, by inserting the disposable tip outlet 410 into the sample and operating the syringe pump 132 to draw sample into the disposable tip 402 (FIG. 4C). As will be appreciated by those knowledgeable in the art, operation of the syringe pump 132 allows for a known volume of sample to be loaded. In some embodiments, the sample may be loaded into the disposable tip through the use of a rotary piston pump, a peristaltic pump, a solenoid pump or a reciprocating piston pump.

Figure 5:
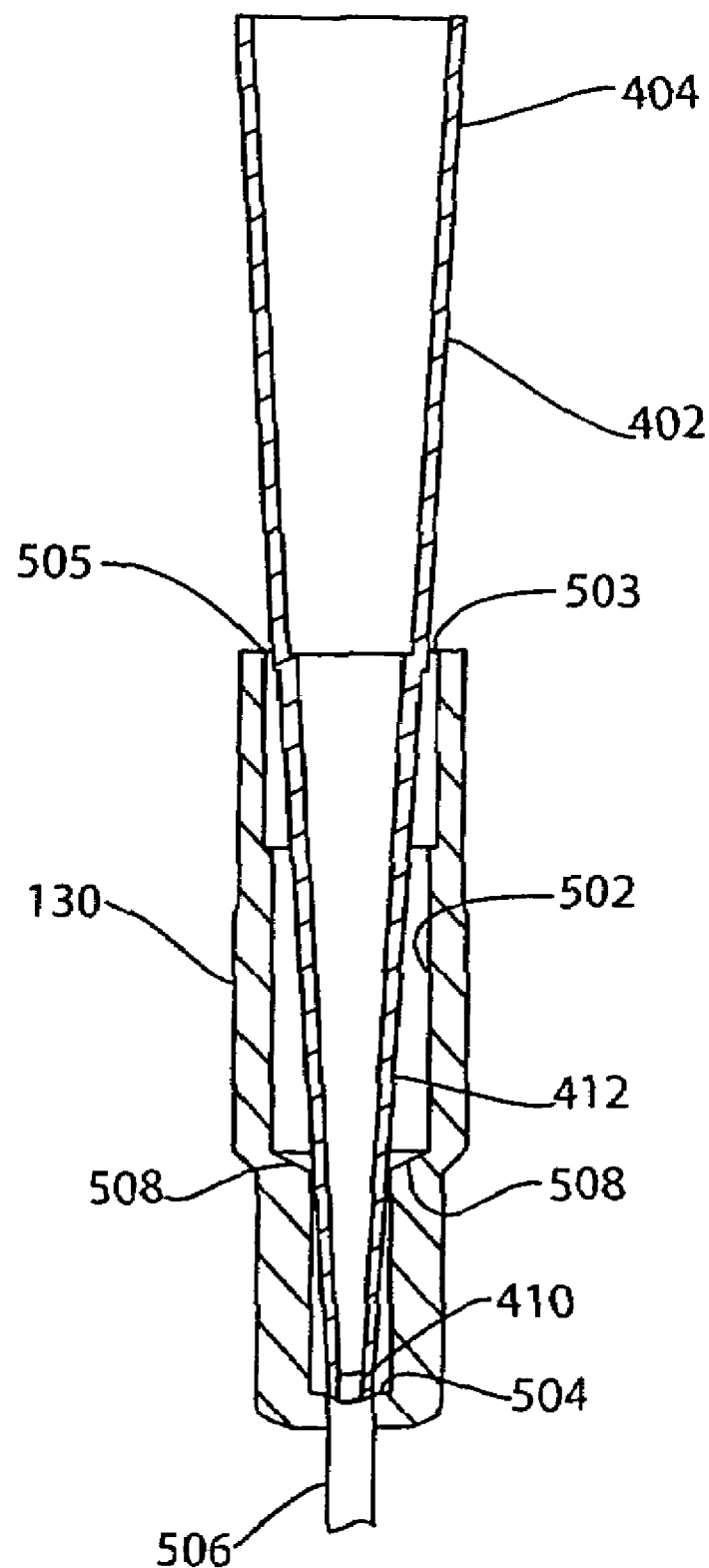
FIG. 5 is a simplified cross sectional view of a disposable tip and injection port.

With reference now made to FIGS. 1 and 4C, as well as to the flowchart of FIG. 3, following loading of the sample into the disposable tip 402 one embodiment of the method includes moving the probe 120 and disposable tip 402 with the automated liquid handler 112 to an injection position adjacent to the injection port 130 and then inserting the disposable tip 402 into the injection port 130 (block 308). FIG. 5 is a cross section of an injection port 130 with a disposable tip 402 inserted therein. Generally, the injection port 130 includes an interior passage 502 adapted to receive the disposable tip 402. As one of skill in the art will understand, although the interior passage shown in FIG. 5 is cone shaped, any interior passage capable of allowing insertion of a disposable tip may be used. An injection port base 504 is defined at the end of the interior passage 502 against which the disposable tip outlet 410 comes into engagement when the disposable tip 402 is inserted. As understood by the skilled artisan, any injection port that provides the advantages of the invention is anticipated. Also as understood by one skilled in the art, the injection port may be made of any biocompatible material. As non-limiting examples, these materials may include polyetheretherketone (PEEK) or titanium.

The disposable tip and the injection port opening 503 form a radial seal 505. By changing the diameter of the injection port opening 503 or the size of the disposable tip being used, the radial seal 505 may be altered to any number of positions without destroying the advantages of the invention. As a non-limiting example, the radial seal 505 may be moved to contact a point closer to the disposable tip outlet of the disposable tip or closer to the probe insertion end of the disposable tip to either provide less dead volume or more dead volume, respectively. As long as the radial seal 505 seals the disposable tip in the injection port, a radial seal in any position may be used. As it is the interior passage of the injection port that provides the advantages of the invention, the skilled artisan will understand that the exterior of the injection port may take any form. In some embodiments, it may be advantageous for the exterior of the injection port to be only slightly greater in size than the interior passage. However, in other embodiments, the exterior of the injection port may be significantly larger than the interior passage. A fluid communication line 506 penetrates the injection port base 504, and leads to the HPLC module 128 shown in FIG. 1. In one embodiment, the interior passage 502 includes an annular shoulder 508 that is near the injection port base 504. In many embodiments, the annular shoulder 508 is no more than about 0.25 inches from the injection port base 504.

Another method of the invention includes sealingly engaging the disposal tip wall 412 within the interior passage 502, and preferably with the annular shoulder 508. Once the disposable tip 402 is inserted and sealingly engaged with the interior passage 502, methods of the invention include the subsequent step of injecting the sample (block 310). As discussed with reference to the schematic of FIG. 2, the sample may be injected through application of a pressure differential by the syringe pump 132. In some embodiments, the sample may be injected into the injection port through the use of a rotary piston pump, a peristaltic pump, a solenoid pump or a reciprocating piston pump.

Inserting the disposable tip 402 into the injection port 130 using the methods and apparatus of the present invention provides valuable benefits and advantages. For example, the present invention deceases the amount of sample loop volume required in the injection system. Generally, in an HPLC system, the test sample volume may be referred to as the sample loop volume. It is desirable when testing a sample to insure that the entire sample loop volume contains test sample, and that no foreign material such as air or an inert pad gas is present. This can be difficult when loading the sample into an injection port using vacuum or positive pressure because there is a chance that some air or other pad gas will be drawn into the injection port and into the sample loop volume receptacle. Dead space present in the injection port during loading increases the risk of gas or air being drawn in.

To minimize this risk, previous methods typically required loading four or more times the sample loop volume into the probe to minimize dead space. Through methods of the present invention, however, it has been discovered that accurate results may be obtained when loading only about two times the sample loop volume. As a non-limiting hypothesis, it is believed that the lowered requirement of sample loop volume is primarily a result of the generally cooperating configuration of the disposable tip 402 and the injection port 130. For example, it is believed that sealingly engaging the disposal tip wall 412 and the annular shoulder 508 substantially minimizes dead space.

It will be appreciated that other methods of the invention may include steps of using disposable tip and interior passage configurations that are different from those illustrated in FIG. 5. An interior passage that more closely mates with the shape of the disposable tip than that shown in FIG. 5 may prove useful in further minimizing or even eliminating dead space. In many embodiments, the configuration of the interior passage generally shown in FIG. 5 will be used because it allows use with current models of standard, non-disposable tips as well as use with many standard cone shaped disposable tips.

Referring again to FIG. 3, following injection of the sample a test is performed on the sample (block 312). In many embodiments, this test will consist of high performance liquid chromatography. Following the injection of the sample, the method demonstrated in FIG. 3 may also includes injecting a solvent rinse to rinse the injection port 130 in preparation for a subsequent test (block 314). In one method, the step following rinsing the injection port includes using the automated liquid handler to move the probe and disposable tip to a disposal position proximate to a waste receptacle (block 316). In the method shown in FIG. 3, the disposable tip will then be removed and deposited into a waste receptacle (block 318).

Figure 6:
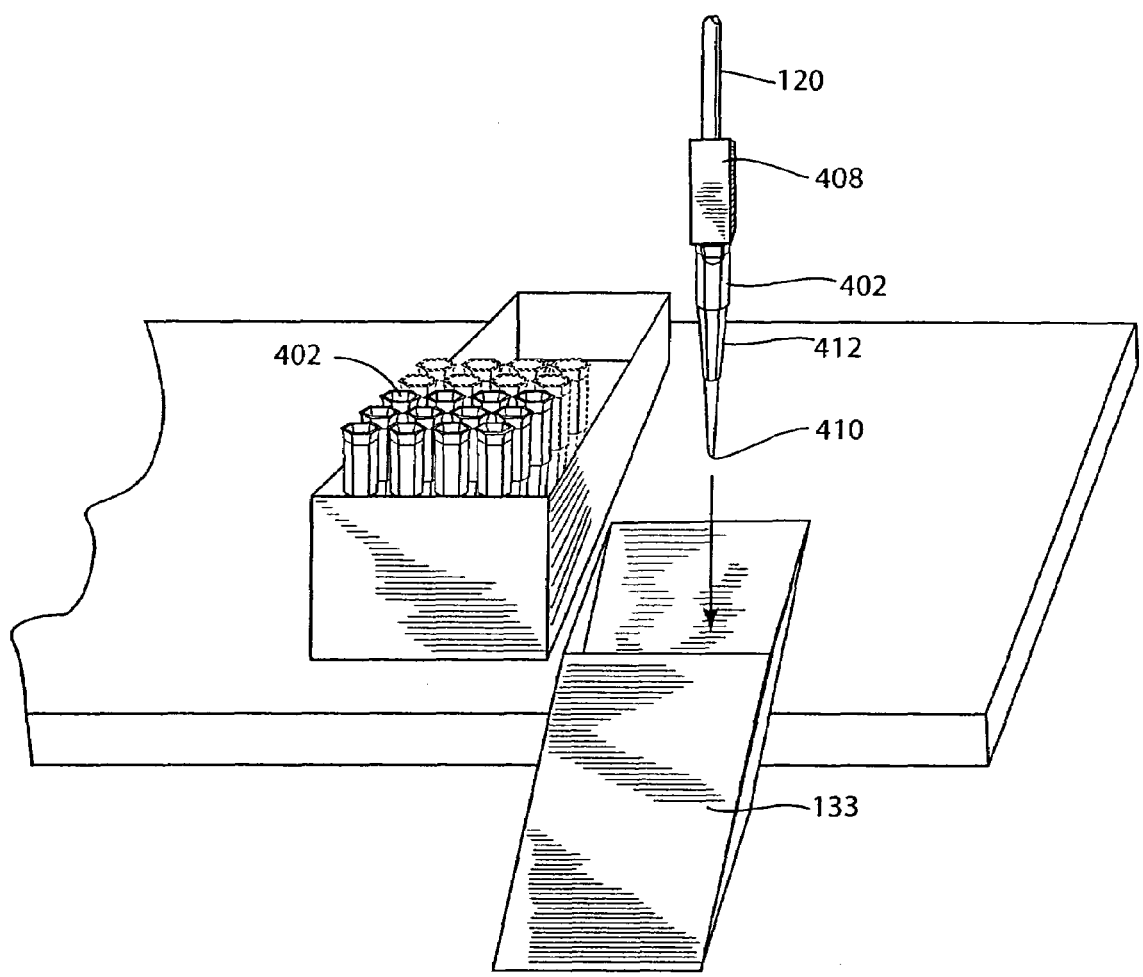
FIG. 6 shows a portion of the HPLC system of FIG. 1 and illustrates removing the disposable tip from the probe.
Figure 7:
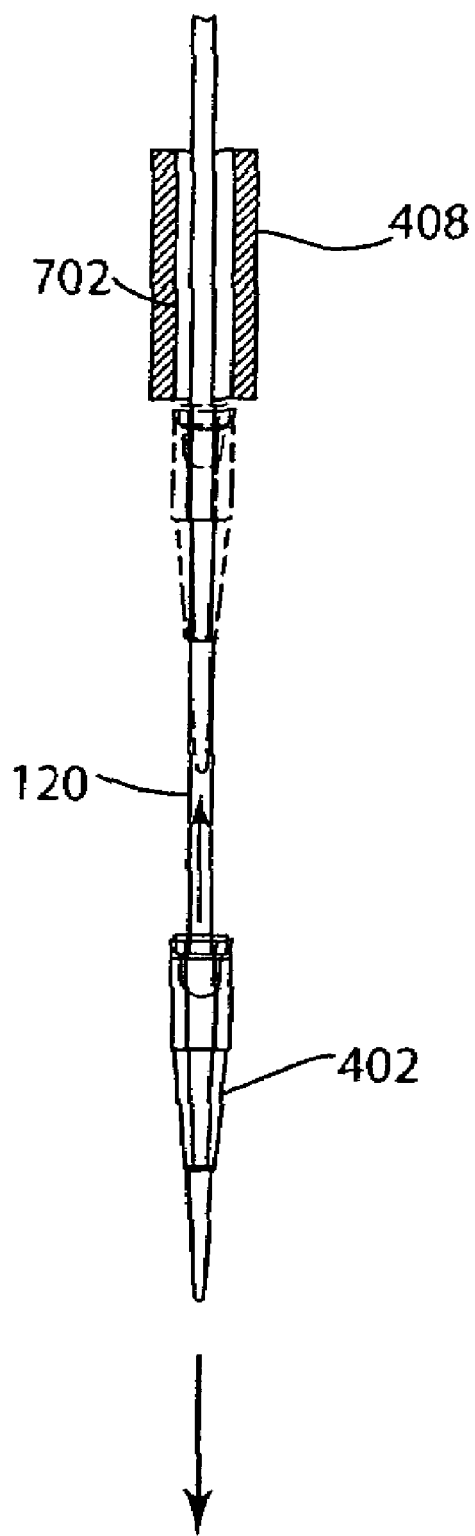
FIG. 7 demonstrates a close-up of the probe guide.

FIG. 6 is useful to illustrate the removal of the disposable tip and the depositing of the disposable tip in the waste receptacle. FIG. 6 demonstrates the probe 120 with the disposable tip 402 mounted thereon above the waste receptacle 133. As demonstrated in FIG. 7, the probe 120 slideably passes through a passage 702 in the probe guide 408. In many embodiments, this passage 702 will be coaxial. Generally, the diameter of the passage 702 in the probe guide 408 is large enough to allow the probe 120 to slideably pass, but will not allow the disposable tip 402 to pass. Accordingly, to remove the disposable tip 402 from the probe 120, the controller may use the automated liquid handler to move the probe 120 vertically upward through the probe guide passage 702. One of skill in the art will understand that the general shape of the probe guide passage is only limited in that it allows the probe to pass but not the disposable tip. For example, the probe guide passage 702 of the embodiment shown in FIG. 7 may be cylindrical in shape because that is the shape of the probe. However, in alternative embodiments, both the entire probe or a portion of the probe and the probe guide passage may be rectangular in shape. Further, there is no requirement that the probe guide passage and the probe be the same shape as long as the probe can travel through the probe guide up to the attachment point of the disposable tip.

The probe guide may contain greater than one probe guide passage. For example, the probe guide may contain two or greater, three or greater, or four or greater probe guide passages. Generally the number of probe guide passages in the probe guide will correspond to the number of probes being used with the methods of the invention. However, one of skill in the art will understand that the number of probe guide passages may be greater than the number of probes being used with the method. When the disposable tip 402 comes into contact with the probe guide 408, the disposable tip 402 will be forced off of the probe 120 and fall into the waste receptacle 133 therebelow. In some embodiments, the probe will come completely through the probe guide during removal of the disposable tip. In other embodiments, the probe will only come far enough through the probe guide to remove the disposable tip. Generally, the probe guide will be integral to the automated liquid handler. In some embodiments, the probe guide will be reversibly attached to the automated liquid handler. In ejecting the tip, either the probe guide may move along the length of a stationary probe or the probe may move through a stationary probe guide. In some embodiments, both movements are envisioned.

Generally the probe guide may be made from any material strong enough to allow removal of the disposable probe tip when the disposable probe tip comes into contact with the probe guide. As a non-limiting example, the probe guide may be made from materials such as stainless steel.

In the embodiment demonstrated in FIG. 3, following removal of the disposable tip 402, a next step includes repeating the steps of blocks 302-318 if more samples are to be tested (block 320), and finally finishing when all samples have been tested (block 322). The method shown in FIG. 3 may therefore be useful to sequentially load a series of test samples into one or more HPLC modules 128.

Valuable advantages and benefits are realized through practice of the invention such as described in FIG. 3. These advantages may include but are not limited to significantly reducing carryover of one sample to another between sequential tests and in some cases even substantially eliminating carryover. Indeed, it has been discovered that through practice of the invention that carryover between tests may be achieved of below about 0.005% (sample mass). In many embodiments, carryover is achieved at a level that is undetectable and therefore substantially eliminated.

Another example benefit and advantage realized through methods of the invention relates to volumetric accuracy of sample volumes and to minimizing variations in volume between tests. For liquid chromatography and many other chemical testing applications, test results may be affected by the volume of the sample tested. For this and other reasons, consistent test sample volumes between tests are desirable. It has been discovered that methods of the invention provide for a very low variation between test sample volumes. The relative volumetric variation between a series of test sample loadings may be expressed as the coefficient of variation (CV), which is a statistical measure of the deviation of a variable from its mean.

As used herein, the deviation is the standard deviation of a particular sample volume and the mean is the mean actual volume of a series of test samples that were desired to be of the same volume. It has been discovered that methods of the invention may achieve a CV of less than about 1%, and more preferably less than about 0.5%. As a non-limiting theory, it is believed that these advantages and benefits result from steps of using a disposable tip made of polypropylene or other hydrophobic material that resists sample hold-up on its walls, steps of using a disposable tip with a conical or other shape that minimizes wetted wall area, and other reasons.

Those knowledgeable in the art will appreciate that methods of the invention may also lead to numerous other benefits and advantages. Also, those knowledgeable in the art will appreciate that the embodiment method of the invention shown and described herein is but one embodiment, and that many equivalent and alternative methods exist within the scope of the invention. Although some variations have been described, many additional variations of the apparatus described within also exist within the scope of the invention. Accordingly, discussion made herein should not be interpreted as a limitation on the scope of the claimed invention. For example, although a method of the invention has been discussed specifically in relation to HPLC, it will likely apply to other testing methods that use liquid chromatography as well as additional instrumentation.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

All references, patents and publications disclosed herein are specifically incorporated by reference thereto. Unless otherwise specified, "a" or "an" means "one or more".

While the present invention has been described with reference to the details of the embodiments of the invention shown in the drawings, these details are not intended to limit the scope of the invention as claimed in the appended claims.

What is claimed is:

1. An automated liquid handler comprising:
   a probe drive system;
   a probe mounted on an arm of the probe drive system;
   a syringe pump operably coupled to the probe;
   a controller operably coupled to the syringe pump to cause aspiration of a sample into the probe; and
   an injection port comprising
      an injection port opening, wherein the injection port opening is configured to accept a disposable tip mounted on the probe;
      an interior passage extending from the injection port opening;
      an injection port base integral with the interior passage and opposite the injection port opening, the injection port base including an opening; and
      an annular shoulder positioned in the interior passage between the injection port opening and the injection port base, the annular shoulder configured to sealingly engage the disposable tip.

2. The automated liquid handler of claim 1 wherein the annular shoulder provides a radial seal to sealingly engage the disposable tip.

3. The automated liquid handler of claim 1 wherein the annular shoulder is positioned closer to the injection port base than to the injection port opening.

4. The automated liquid handler of claim 1 wherein the annular shoulder is less than or equal to about 0.25 inches from the injection port base.

5. The automated liquid handler of claim 1 wherein the injection port opening is further configured to sealingly engage the disposable tip.

6. The automated liquid handler of claim 1 further comprising a plurality of probes mounted on the arm of the probe drive system and operably coupled to the syringe pump.

7. The automated liquid handler of claim 6 further comprising a plurality of injection ports, associated with the plurality of probes.

8. A liquid chromatography sample injection system comprising:
   a probe drive system;
   a probe mounted on an arm of the probe drive system;
   an injection port opening, wherein the injection port opening is configured to accept a disposable tip mounted on the probe;
   an interior passage extending from the injection port opening;
   an injection port base integral with the interior passage and opposite the injection port opening, the injection port base including an opening;
   an annular shoulder positioned in the interior passage between the injection port opening and the injection port base, the annular shoulder configured to sealingly engage the disposable tip;
   an injector valve;
   a fluid communication line connecting the injection port base with the injector valve;
   a syringe pump operably coupled to the probe; and
   a controller operably coupled to the syringe pump to cause aspiration of a sample into the probe and injection of the sample into the fluid communication line.

9. The liquid chromatography sample injection system of claim 8 wherein the annular shoulder provides a radial seal to sealingly engage the disposable tip.

10. The liquid chromatography sample injection system of claim 8 wherein the annular shoulder is positioned closer to the injection port base than to the injection port opening.

11. The liquid chromatography sample injection system of claim 8 wherein the annular shoulder is less than or equal to about 0.25 inches from the injection port base.

12. The liquid chromatography sample injection system of claim 8 wherein the injection port opening is further configured to sealingly engage the disposable tip.

13. The liquid chromatography sample injection system of claim 8 further comprising a workbed and a waste receptacle reversibly attached to the workbed, wherein the waste receptacle is adapted to collect the disposable tip after injection of the sample into the fluid communication line.

14. The liquid chromatography sample injection system of claim 8 further comprising a probe guide coupled to the probe, the probe guide comprising a passage coaxial with the probe, wherein the passage allows the probe to vertically slide through but does not allow the disposable tip to vertically slide through, thereby removing the disposable tip from the probe.

* * * * *